(12) United States Patent
Adami et al.

(10) Patent No.: US 7,053,239 B2
(45) Date of Patent: May 30, 2006

(54) METHOD FOR PRODUCING METHYL FORMATE

(75) Inventors: Christoph Adami, Weinheim (DE); Michael Slany, Kirchheim (DE); Jörn Karl, Mannheim (DE); Gerd Kaibel, Lampertheim (DE); Martin Schäfer, Grünstadt (DE); Peter Zehner, Ludwigshafen (DE); Michael Röper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 19 days.

(21) Appl. No.: 10/511,088

(22) PCT Filed: Apr. 15, 2003

(86) PCT No.: PCT/EP03/03902

§ 371 (c)(1),
(2), (4) Date: Oct. 14, 2004

(87) PCT Pub. No.: WO03/089398

PCT Pub. Date: Oct. 30, 2003

(65) Prior Publication Data

US 2005/0143598 A1 Jun. 30, 2005

(30) Foreign Application Priority Data

Apr. 19, 2002 (DE) ................. 102 17 528

(51) Int. Cl.
*C07C 67/36* (2006.01)
(52) U.S. Cl. .................................... 560/232
(58) Field of Classification Search ............... 560/232
See application file for complete search history.

(56) References Cited

U.S. PATENT DOCUMENTS

| | | | |
|---|---|---|---|
| 4,216,339 A | 8/1980 | Couteau et al. | |
| 4,661,624 A | 4/1987 | Chang et al. | |
| 5,917,085 A | 6/1999 | Lippert et al. | |

FOREIGN PATENT DOCUMENTS

| | | | |
|---|---|---|---|
| DE | 863 046 | | 1/1953 |
| DE | 880 588 | * | 6/1953 |
| DE | 926 785 | | 4/1955 |
| DE | 1 046 602 | | 12/1958 |
| DE | 1 147 214 | | 4/1963 |
| EP | 0 251 112 | | 1/1988 |
| WO | WO 96/26178 | | 8/1996 |

OTHER PUBLICATIONS

Ullmann's Encyclopedia of Industrial Chemistry, Sixth Edition, 2000 Electronic Release Formic Acid—Production (Werner Reutemann, Heinz Kieczka).

P. Zehner, M. Krause: Ullmann's Encyclopedia of Industrial Chemistry, Sixth Edition 1999 Electronic Release: Chapter "Bubble Columns" 1999, WILEY-VCH, Weinheim, Germany XP002248747, Kapitel 2.3 bis 2.6 sowie die Abbildungen 7 und 11.

* cited by examiner

*Primary Examiner*—Paul A. Zucker
(74) *Attorney, Agent, or Firm*—Novak Druce & Quigg, LLP; Jason D. Voight

(57) ABSTRACT

The invention relates to a process for the preparation of methyl formate by reacting methanol with carbon monoxide at a pressure of from 0.5 to 10 MPa abs. and a temperature of from 50 to 150° C. in the presence of a metal alkoxide as catalyst in a reactor, in which a gas stream is withdrawn from the reactor, entrained methyl formate is removed from this gas stream by condensation, and all or some of the remaining gas stream is returned to the reactor as circulating-gas stream and a mean gas superficial velocity of from 1 to 20 cm/s is set in at least one region of the reactor in which the gas flows essentially in one direction.

9 Claims, 3 Drawing Sheets

METHOD FOR PRODUCING METHYL FORMATE

The present invention relates to a process for the preparation of methyl formate by reacting methanol with carbon monoxide at a pressure of from 0.5 to 10 MPa abs. and a temperature of from 50 to 150° C. in the presence of a metal alkoxide as catalyst in a reactor, in which a gas stream is withdrawn from the reactor, entrained methyl formate is removed from this gas stream by condensation, and all or some of the remaining gas stream is returned to the reactor as circulating-gas stream.

Methyl formate (formic acid methyl ester) is an important intermediate in the manufacture of formic acid and is produced in industry by continuous carbonylation of methanol in the liquid phase in the presence of sodium methoxide or potassium methoxide as catalyst at temperatures in the range from about 50 to 150° C. (see Ullmann's Encyclopedia of Industrial Chemistry, $6^{th}$ edition, 2000 electronic release, Chapter "FORMIC ACID—Production"). The reaction is a homogeneously catalyzed equilibrium reaction in which the equilibrium is shifted toward methyl formate with increasing carbon monoxide partial pressure and falling temperature. The known processes are operated at a pressure of up to 30 MPa abs. and a temperature of from 50 to 150° C.

In the said preparation of methyl formate, two undesired side reactions occur in particular, which can result in severe problems in the continuously operated process. Both side reactions result in the formation of alkali metal formate. Thus, the alkali metal methoxide employed reacts in a hydrolysis reaction with any traces of water that may have been introduced, giving alkali metal formate and methanol. Furthermore, the alkali metal methoxide employed also reacts with methyl formate present to form alkali metal formate and dimethyl ether. The alkali metal formate can then result in deposits in the apparatuses and piping, or even blockage of pipes and valves, owing to its inadequate solubility in the reaction medium. The risk of salt precipitation is particularly great if the methanol conversion is high and consequently the concentration of methyl formate is high, and can therefore in principle be reduced by establishing a partial conversion, ensuring a low concentration of methyl formate. However, this is countered by the aim of achieving the highest possible space-time yield and thus instead establishing a high concentration of methyl formate.

A multiplicity of processes and process variants are discussed in the literature, differing through different measures for reducing the tendency toward the formation of deposits.

Thus, DE patent specification 926 785 describes a high-pressure process which operates at 30 Mpa, in which only a low catalyst concentration of 0.25% by weight of sodium (corresponding to 0.59% by weight of sodium methoxide) is employed in order to reduce salt deposition. In addition, the reactor contents are stirred continuously in order to keep the deposited salt in suspension. The liquid discharge from the reactor, which comprises about 90% of methyl formate, is decompressed and worked up by distillation.

DE-B 1 046 602 describes a continuous, two-step process in the presence of from 0.5 to 5% by weight of alkali metal methoxide at a pressure of from 5 to 30 MPa. The aim here is to prevent deposition by ensuring turbulent flow in the reactor. The overall conversion of methanol is about 90%. The liquid discharge from the reactor is decompressed and worked up by distillation.

DE-B 1 147 214 describes a high-pressure process which operates at from 15 to 20 Mpa, in which the reaction is carried out in the presence of from 0.12 to 0.3 mol % of alkali metal methoxide in at least two successive reaction zones which are characterized by decreasing temperatures, and the carbon monoxide is fed to the reactor at different heights in at least two sub-streams. It is intended here to prevent sedimentation of the salt-like precipitates by short-duration, recurring changes in the carbon monoxide mixing ratios. The overall conversion of methanol is up to 97%. The liquid discharge from the reactor is decompressed and worked up by distillation.

WO 96/26178 describes a high-pressure process in which the reaction is carried out in the presence of from 0.05 to 0.2% by weight of alkali metal methoxide at a pressure of from 21 to 25 MPa. Due to the good dispersion of the carbon monoxide, for example through a jet nozzle, an adequately high conversion can be achieved in spite of the low catalyst concentration. Thus, the concentration of methyl formate in the discharge from the reactor is up to 97% by weight. The liquid discharge from the reactor is decompressed and worked up by distillation.

DE-A 2 243 811 describes a process in which the reaction is carried out in the presence of from 0.4 to 1.5% by weight of alkali metal methoxide under countercurrent conditions at a pressure of from 4 to 30 MPa and which has a plurality of reaction zones connected in series. The preferred apparatuses are, in particular, columns having flooded trays. The reaction mixture formed at the bottom of the column comprises from 20 to 70% by weight of methyl formate and is worked up by distillation after decompression.

EP-A 0 617 003 describes a process in which the reaction is carried out in the presence of from 0.4 to 1.5% by weight of alkali metal methoxide at a pressure of from 1 to 30 MPa. Firstly, the reactants are combined in a mixing zone and at least partially reacted. The resultant reaction solution is subsequently saturated with carbon monoxide and fed to a post-reaction zone without the feed of further starting materials. The liquid discharge from the reactor is decompressed and worked up by distillation.

WO 01/07392 describes a process in which the reaction is carried out in the presence of from 0.05 to 0.5% by weight of alkali metal methoxide at a carbon monoxide pressure of from 9 to 18 MPa. The liquid discharge from the reactor, which comprises from about 60 to 95% by weight of methyl formate, is fed to a distillation column in order to remove the methyl formate. The catalyst- and methanol-containing bottom stream that remains is recycled again, with residual catalyst and catalyst degradation products being removed from a sub-stream thereof via a desalination device. In the working examples, space-time yields in the range from 370 to 880 g/lVh of methyl formate were achieved.

All the above-mentioned processes have the crucial disadvantage of a high reaction pressure of up to 30 MPa, which requires high equipment complexity, high investment costs and high energy costs as a consequence of the requisite compression. Further disadvantages arise from the individual measures mentioned. Thus, for example, stirring under high pressure, as proposed in DE 926 785, is a technical problem which cannot be solved in practice. The short-duration changes in the carbon monoxide sub-streams that are proposed in DE 1 147 214 require complex monitoring and control efforts and may result in unstable states in the reactor. In addition, the said measures at best enable a reduction in, but not prevention of, the formation of salt-like deposits. The low concentrations of methyl formate in the reaction product stream which are obtainable according to the teaching of DE-A 2 243 811, EP-A 0 617 003 and WO 01/07392 require the handling of large volume streams and result in high energy expenditure during removal of the methyl formate by distillation and thus result in a particularly unfavorable energy balance for the process as a whole.

U.S. Pat. No. 4,661,624 discloses a two-step process with recycling of the catalyst-containing, methanolic solution. The reaction is carried out at a pressure of from 0.48 to 6.9 MPa (from 70 to 1000 psia) and an alkali metal methoxide concentration of from 1 to 8 mol % (corresponding to from 1.7 to 13.5% by weight of sodium methoxide). In the second step, further methanol is supplied under countercurrent conditions in order to react the remainder of the carbon monoxide. The process is operated at an extremely low conversion, and consequently the liquid discharge from the reactor comprises only from about 2 to 20 mol % of methyl formate. It is fed to a distillation column in order to remove the methyl formate. The catalyst- and methanol-containing bottom stream which remains is recycled again. The consequently very high concentration of methanol in the reaction mixture counteracts deposition of salt-like deposits. However, this process has the disadvantages of the large amount of energy consequently needed for removal of the methyl formate by distillation and the handling of large volume streams as a consequence of the high dilution factor, giving rise overall to an unfavorable energy balance for the process as a whole. Furthermore, large amounts of fresh catalyst have to be supplied continuously in order to maintain the high catalyst concentration that is necessary.

U.S. Pat. No. 4,216,339 teaches a process in which the reaction is carried out in the presence of from 0.2 to 4% by weight of alkali metal methoxide at a pressure of from 2 to 11 MPa and in which the supplied carbon monoxide is dispersed in the liquid reaction mixture via a self-priming jet nozzle which is operated by a sufficiently large circulating stream. In accordance with the amount of starting materials supplied, a corresponding amount of reaction mixture is removed continuously from the liquid circulating stream and, after decompression, worked up by distillation. In Example 2, a concentration of methyl formate of 51% by weight was obtained at a pressure of 4.4 MPa in the reaction mixture. This process likewise has the disadvantage of high energy expenditure, as a consequence of the high dilution, for removal of the methyl formate from the reaction mixture by distillation. Furthermore, a large volume stream of the reaction mixture has to be pumped continuously around the circuit. In overall terms, therefore, an unfavorable energy balance arises for the process as a whole.

German Patent 863 046 teaches a continuous low-pressure process in which methanol and from 1 to 2% by weight of sodium (corresponding to from 2.3 to 4.7% by weight of sodium methoxide) are transported from top to bottom in a bubble column fitted with packing elements, and carbon monoxide is transported from bottom to top in countercurrent and reacted at a pressure of from about 2.5 to 3.0 MPa (from 25 to 30 atmospheres). The reaction mixture is removed continuously from the bottom of the reactor and worked up by distillation. The gas removed from the top of the reactor is passed through a condenser, freed from entrained methyl formate in a separator, and, mixed with fresh carbon monoxide, fed back to the reactor in order to ensure an adequately large gas-treatment stream. The methyl formate condensed out of the gas phase in the separator is likewise worked up by distillation. The pressure and temperature should be set in such a way that the catalyst and degradation products thereof are kept in solution.

An improved process compared with DE 863 046 is described in German Patent 880 588. In this improved low-pressure process, methanol and from 1.6 to 2.5% by weight of sodium (corresponding to from 3.8 to 5.9% by weight of sodium methoxide) are transported from bottom to top in co-current with carbon monoxide in a bubble column fitted with packing elements and reacted at a pressure of up to 3.0 MPa (up to 30 atmospheres). Liquid reaction mixture is removed from a gas dome located at the top of the reactor and fed back to the bottom of the reactor via a circulating pump. The gaseous phase is withdrawn at the upper end of the gas dome, passed through a condenser, subsequently freed from entrained methyl formate in a separator and, mixed with fresh carbon monoxide, fed back to the reactor in order to ensure an adequately large gas-treatment stream. In contrast to the process described in DE 863 046, all the methyl formate is removed via the gas phase and, after condensation, worked up by distillation.

The example contained in DE 880 588 states that 3.1 kg of methyl formate can be obtained per hour using the 770 l reactor (length 8 m and internal diameter 35 cm) at 3.0 MPa and from 85 to 88° C. in continuous operation. This corresponds to a space-time yield of only 4 g/lVh of methyl formate. The methyl formate concentration in the condensed crude discharge was about 60% by weight (from 38 to 40% by weight of methanol). A gas superficial velocity of about 0.21 cm/s arises from the amount of circulated gas of 206 $cm^3/s$, calculated under reaction conditions (corresponding to 17 $m^3$ at 0° C. and 0.1 MPa), and the reactor cross section of 962 $cm^2$.

The process described has the disadvantage of a very low space-time yield of 4 g/lVh of methyl formate, which is about two orders of magnitude below the values achieved in the high-pressure processes, the very high catalyst concentration of from 3.8 to 5.9% by weight of sodium methoxide, and the high consumption of catalyst. The process described therefore operates very uneconomically.

It is an object of the present invention to find a process for the preparation of methyl formate by reaction of methanol with carbon monoxide which does not have the above-mentioned disadvantages, is technically simple to carry out, results in only very slight deposition of salt-like deposits, or none at all, has low investment costs, low energy consumption and low consumption of catalyst, and facilitates a space-time yield of methyl formate of $\geq$100 g/lVh.

We have found that this object is achieved by a process for the preparation of methyl formate by reacting methanol with carbon monoxide at a pressure of from 0.5 to 10 MPa abs. and a temperature of from 50 to 150° C. in the presence of a metal alkoxide as catalyst in a reactor, in which a gas stream is withdrawn from the reactor, entrained methyl formate is removed from this gas stream by condensation, and all or some of the remaining gas stream is returned to the reactor as circulating-gas stream, which comprises setting a mean gas superficial velocity of from 1 to 20 cm/s in at least one region of the reactor in which the gas flows essentially in one direction.

In the process according to the invention, a mean gas superficial velocity of from 1 to 15 cm/s, particularly preferably from 2 to 10 cm/s and very particularly preferably from 5 to 10 cm/s, is preferably set in at least one region of the reactor in which the gas flows essentially in one direction.

The term 'gas superficial velocity' is taken to mean the quotient of the volume flow rate of the gas flowing in this region and the free cross-sectional area of the reactor region in question. The volume flow rate of the gas flowing in this region means the total gas flow rate under the given pressure and at the given temperature. The free cross-sectional area is taken to mean the cross-sectional area that is accessible to the fluid reaction medium. The part of any internals present that is not accessible to the fluid reaction medium is not counted as part of the free cross-sectional area. It should be pointed out that the liquid fraction present in the reactor region in question is not taken into account when calculating the gas superficial velocity in accordance with the definition.

If the reactor is, for example, a bubble-column reactor, the gas is generally introduced in the lower part of the reactor, with the flow direction of the gas in the reaction medium being essentially directed upward owing to the upward force. The bubble-column reactor therefore generally contains only a single region with respect to the flow direction of the gas.

If the reactor is, for example, a so-called jet loop reactor, the gas is introduced through a nozzle into a tube inserted centrally in the reactor. In addition, further gaseous and liquid reaction medium is conveyed into the inserted tube by the introduced pulse and induces a reactor-internal circuit. The reaction medium flows through the inserted tube, is deflected by a so-called baffle plate at the end of the tube, flows between the inner reactor wall and the inserted tube in the opposite direction and is finally deflected again by the pulse generated by the nozzle and again drawn into the inserted tube. The jet loop reactor thus generally contains two regions with respect to the flow direction of the gas, namely a region inside the inserted tube and a region outside the inserted tube, in which the gas flows in opposite directions, at least one of these two regions having a mean gas superficial velocity of from 1 to 20 cm/s in the process according to the invention.

In the process according to the invention, the catalyst employed is a metal alkoxide or a mixture of various metal alkoxides.

In general, the reaction is carried out at a concentration of catalyst employed of from 0.01 to 2 mol/kg of liquid reaction mixture, preferably from 0.02 to 1.5 mol/kg of liquid reaction mixture and particularly preferably from 0.8 to 1.2 mol/kg of liquid reaction mixture. The term 'concentration of catalyst employed' is taken to mean the total of the concentrations of metal alkoxide and its secondary products, such as, in particular, the metal formate formed in an undesired side reaction.

As suitable metal cations of the metal alkoxates, mention may be made of the cations of the metals from groups 1 to 15 of the Periodic Table. Suitable metals are, for example, alkali metals, alkaline-earth metals and aluminum. Preference is given to the alkali metals and alkaline-earth metals and particularly preferably the alkali metals. As very particularly preferred metals, mention may be made of sodium and potassium, in particular potassium.

As suitable alkoxide anions, mention may be made of alkoxide anions having from 1 to 12 carbon atoms, preferably unbranched or branched $C_1$- to $C_{12}$-alkoxide anions, for example methoxide, ethoxide, 1-propoxide, 2-propoxide, 1-butoxide, 2-butoxide, 2-methyl-1-propoxide, 2-methyl-2-propoxide, 1-pentoxide, isoamyloxide, 1-hexoxide, 1-heptoxide, 1-octoxide, 1-nonoxide and 1-decoxide. As particularly preferred alkoxide, mention may be made of methoxide.

The catalyst employed in the process according to the invention is preferably sodium methoxide or potassium methoxide, in particular potassium methoxide.

In the process according to the invention, the reaction of methanol with carbon monoxide in the presence of the metal alkoxide as catalyst is preferably carried out at a temperature of from 50 to 110° C., particularly preferably from 60 to 100° C. and very particularly preferably from 60 to 85° C. Reaction temperatures of from 60 to 85° C. surprisingly result in an increased carbon monoxide conversion compared with reaction temperatures above 85° C., with the same residence time. The reaction is preferably carried out at a pressure of from 0.5 to 6 MPa abs., particularly preferably from 1 to 5 MPa abs. and very particularly preferably from 2 to 4 MPa abs.

The molar ratio between the total amount of methanol fed to the reactor and the amount of freshly supplied carbon monoxide in the process according to the invention is generally from 1 to 5. The said molar ratio is preferably from 1 to 4 and very particularly preferably from 1.4 to 3.3.

The methanol fed to the reactor is composed of the freshly supplied methanol and any recycled methanol.

It should be pointed out that the above-mentioned molar ratio is based on the amount of freshly supplied carbon monoxide. Since a carbon monoxide-containing circulating-gas stream is additionally fed back to the reactor in the process according to the invention for the supply of fresh carbon monoxide, the molar methanol/carbon monoxide ratio actually present in the reactor is lower than the above-mentioned molar ratio and is generally in the range from 0.06 to 0.2, depending on the amount of recycled carbon monoxide.

Reactors which can be employed in the process according to the invention are in principle all reactors which are suitable for gas/liquid reactions and in which a mean gas superficial velocity of from 1 to 20 cm/s can be achieved in at least one region of the reactor in which the gas flows essentially in one direction. For the purposes of the terminology used, the term reactor can also be taken to mean a plurality of individual apparatuses connected in series. Suitable apparatuses which may be mentioned are the bubble-column reactor and the loop reactor. Preference is given to the bubble-column reactor and the jet loop reactor. The reactors may, if desired, be fitted with diverse internals, for example packing elements, static mixers or heat exchangers.

The methanol-containing liquid stream and the carbon monoxide-containing gas stream can be supplied in various ways, depending on the nature of the reactor employed. In the case of the use of a bubble-column reactor, the gas stream is generally introduced into the lower region of the reactor using conventional gas injection devices. The methanol-containing liquid stream can be introduced, for example, in the upper region (countercurrent method) or in the lower region (co-current method). On use of a jet loop reactor, the gas stream is generally introduced in the upper region of the reactor, with a downward-facing pulse direction, or in the lower region of the reactor, with an upward-facing pulse direction. The methanol-containing liquid stream can be introduced at one or more points in the reactor.

On use of a bubble column, this is preferably operated under co-current conditions with respect to the feed of the methanol-containing liquid stream and of the carbon monoxide-containing gas stream. The carbon monoxide-containing gas stream and the methanol-containing gas stream are thus introduced in the lower region of the bubble column.

In general, a gas stream is withdrawn continuously at the top of the reactor. This generally comprises methyl formate, unreacted methanol and unreacted carbon monoxide. The entrained methyl formate is removed from this gas stream by condensation, and all or some of the remainder of the gas stream is fed back to the reactor as circulating-gas stream. In a preferred embodiment, the liquid stream which has been condensed out of the withdrawn gas stream and which generally comprises methyl formate and unreacted methanol is separated by distillation, and the methanol obtained is likewise fed back to the reactor.

BRIEF DESCRIPTION OF THE DRAWINGS

FIG. 1 shows a simplified process flow chart of a preferred embodiment for the preparation of methyl formate using a bubble-column reactor with recycling of the carbon monoxide-containing circulating-gas stream and with recycling of a methanol-containing liquid stream. Freshly supplied carbon monoxide (I) is mixed with the recycled circulating-gas stream via line (3) and fed to the bubble-column reactor (B) via a compressor (A). This bubble-column reactor is additionally supplied, via line (7) and compressor (G), with freshly supplied methanol (III), with freshly supplied catalyst (II) and with recycled methanol. In general, the reactor contains a device for the purging of catalyst-containing reaction mixture (VI). A gaseous stream is withdrawn at the top of the reactor via line (1), and entrained methyl formate and entrained methanol are condensed out in a heat exchanger (C). The remaining gas stream is fed back to the reactor via lines (2) and (3), with a device for purging waste gas (V) generally being present. The liquid condensed out in the heat exchanger (C) is fed via line (4) to a condensate tank (D) and from the latter via line (5) into a distillation column (E). The methanol-containing liquid stream produced as bottom product is fed back to the reactor (B) via line (6) and the compressor (F). Methyl formate (IV) is obtained as top product from the distillation column.

Figure 1:
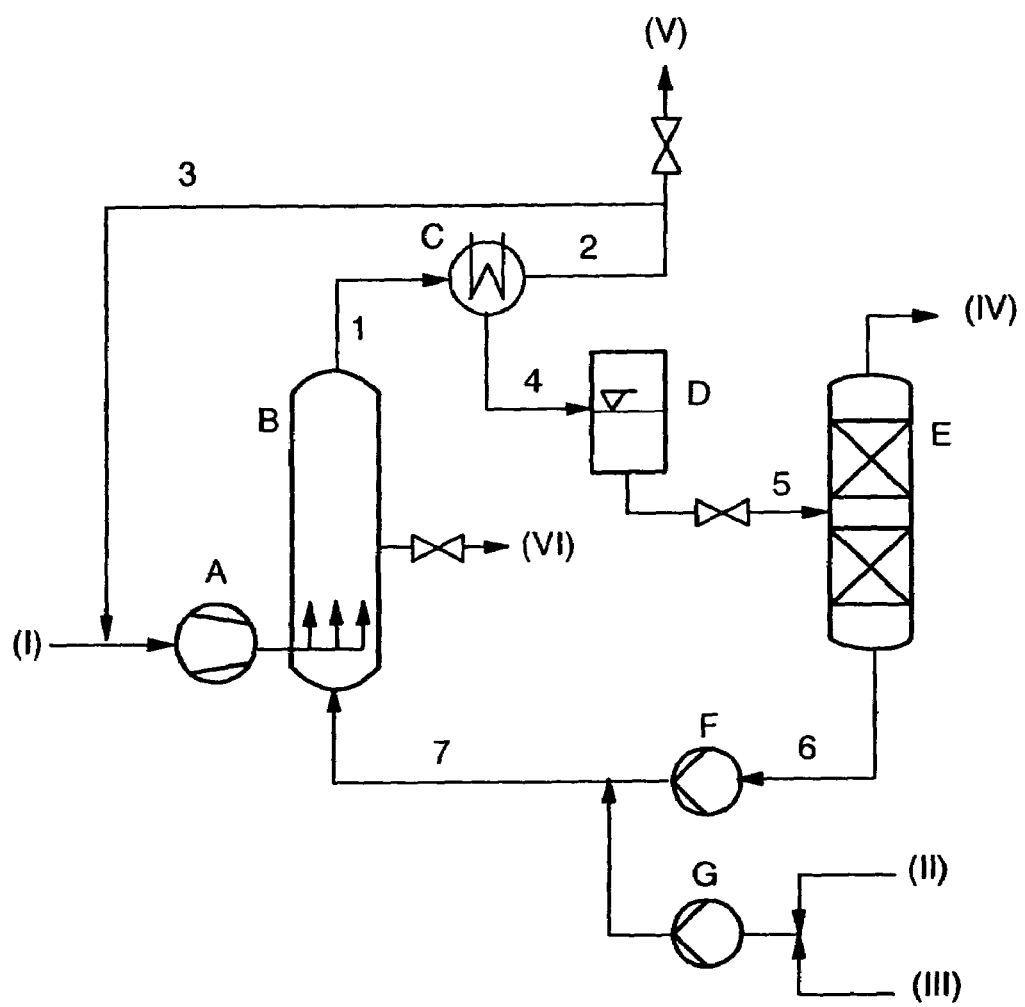
FIG. 1 displays a simplified process flow chart for the preparation of methyle formate using a bubble column reactor with recycling of the carbon monoxide containing circulating gas stream and with recycling of a methanol containing liquid stream.

It should be noted that it is possible for other apparatuses, for example a loop reactor, to be used instead of the bubble-column reactor in the process depicted in FIG. 1.

In order to reduce back-mixing, it is generally advantageous to carry out the reaction in a cascaded reactor. For the purposes of the above reactor definition, the term "cascaded reactor" is also taken to mean a plurality of individual apparatuses connected in series, each of which may, independently of one another, be cascaded or non-cascaded.

Thus, it is possible, for example, to connect a plurality of individual apparatuses, for example bubble columns or loop reactors, in series, where the series may also include different types of apparatus.

As an example of a multi-cascaded apparatus, mention may be made of the cascaded bubble column. This is generally cascaded through sieve trays.

The process according to the invention is particularly preferably carried out using a cascaded reactor in which the uppermost zone is operated at a temperature of from 80 to 150° C. and preferably from 80 to 120° C. The said temperature range facilitates a particularly advantageous evaporation rate of the methyl formate formed. In order to achieve a particularly high carbon monoxide conversion in the preceding zone(s), this/these is/are preferably operated at a reaction temperature of from 60 to 85° C. Since the evaporation in the uppermost zone requires evaporation energy, it is particularly advantageous to introduce this energy by additional heating of the reaction mixture. To this end, reaction mixture is particularly preferably withdrawn from a preceding zone, passed through a heat exchanger and subsequently into the uppermost zone.

The particularly preferred process mentioned in the preceding paragraph has the particular advantage of evaporation of the methyl formate formed at a temperature which ensures a particularly advantageous evaporation rate while the reaction of methanol with carbon monoxide is simultaneously carried out in the presence of a metal alkoxide as catalyst at a temperature which facilitates a particularly high carbon monoxide conversion.

Figure 2:
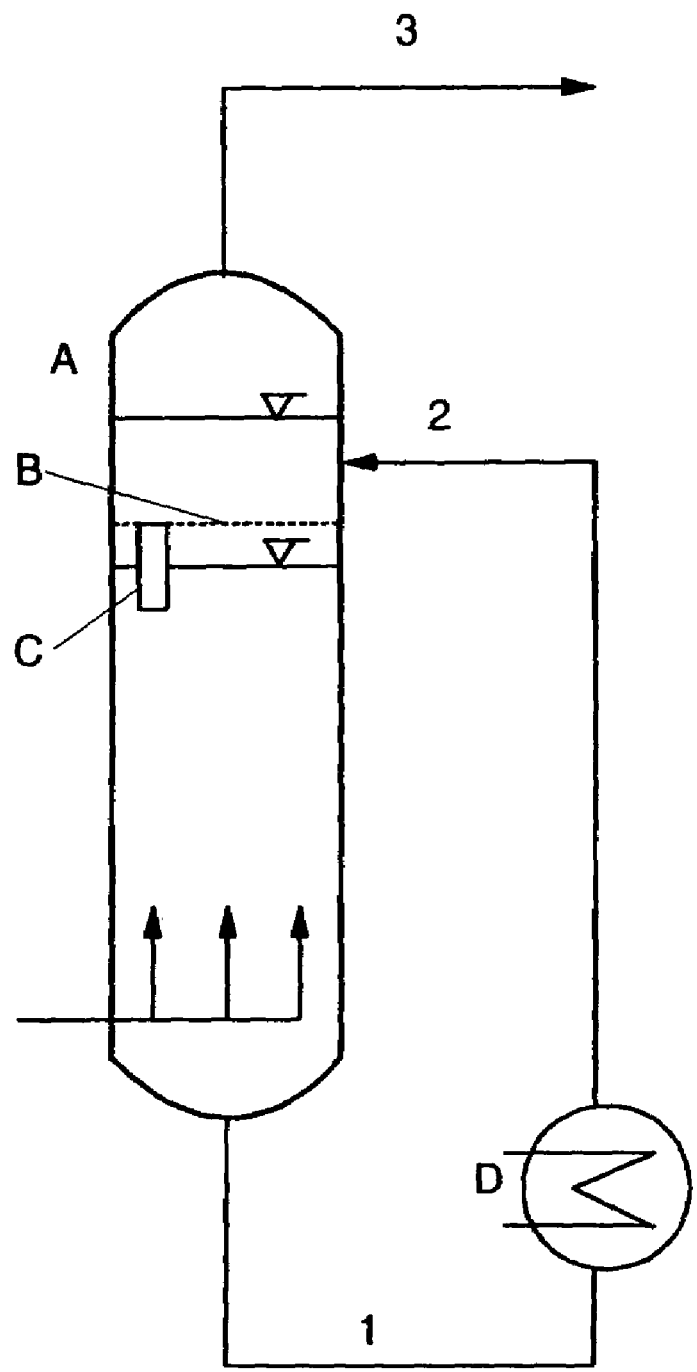
FIG. 2 displays a cascade reactor using the example of a bubble column.

FIG. 2 shows a particularly preferred embodiment of a cascaded reactor through the example of a bubble column, in which reaction mixture is withdrawn in the lower region via line (1), heated in a heat exchanger (D) and fed to the upper zone via line (2). This zone is preferably separated from the preceding zone by a sieve tray (B) with discharge shaft (C). The sieve tray enables the gas flowing out of the preceding zone to pass through, so that it bubbles through the reaction mixture in finely divided form into the uppermost zone and thus promotes the stripping effect. The carbon monoxide-, methyl formate- and methanol-containing gas stream is withdrawn via line (3). The liquid present in the uppermost zone, which does not evaporate, runs back into the preceding zone via the discharge shaft.

An analogous design to that shown in FIG. 2 is in principle also possible on use of other apparatuses, such as a loop reactor.

Very particular preference is given to a process in which the gas stream withdrawn from the reactor is separated in a rectifying column into a methyl formate-containing bottom stream and a carbon monoxide- and methyl formate-containing top stream, entrained methyl formate is removed from the top stream by condensation, and all or some of the remaining gas stream is fed back to the reactor as circulating-gas stream.

Figure 3:
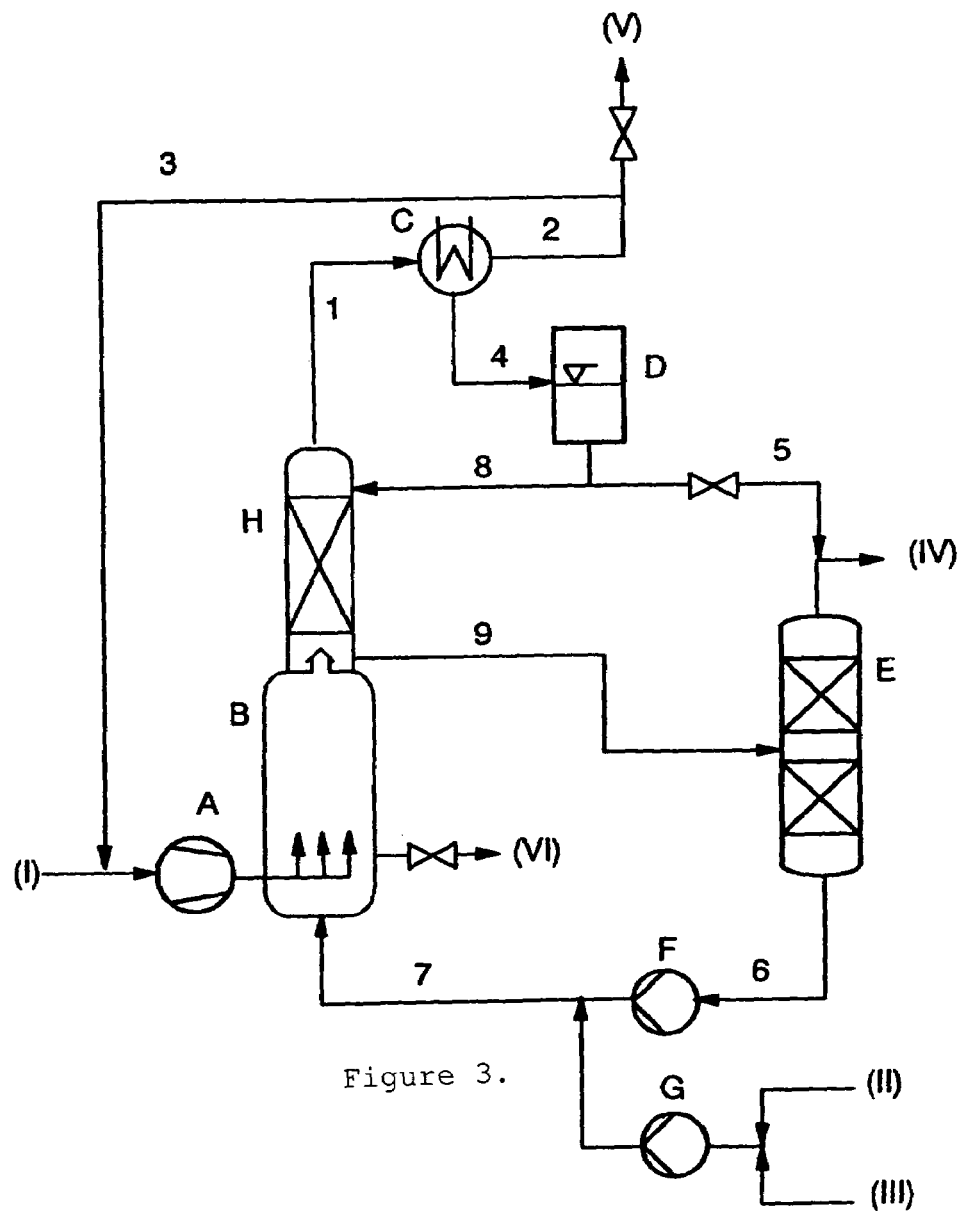
FIG. 3 displays a simplified process flow chart of a preferred embodiment for the preparation of methyl formate using a rectifying column with recycling of the carbon monoxide containing circulating gas stream and with recycling of a methanol containing liquid stream.

FIG. 3 shows a simplified process flow chart of a preferred embodiment for the preparation of methyl formate using a rectifying column with recycling of the carbon monoxide-containing circulating-gas stream and with recycling of a methanol-containing liquid stream. Freshly supplied carbon monoxide (I) is mixed with the recycled circulating-gas stream from line (3) and fed to the bubble-column reactor (B) via a compressor (A). This bubble-column reactor is in addition supplied with freshly supplied methanol (III), with freshly supplied catalyst (II) and with recycled methanol via line (7) and the compressor (G). In general, the reactor contains a device for purging catalyst-containing reaction mixture (VI). A rectifying column (H), which separates the gas stream originating from the reactor into a methyl formate-containing bottom stream and a carbon monoxide- and methyl formate-containing top stream, is located at the top of the reactor. The bottom stream from the rectifying column (H) is passed via line (9) into a distillation column (E). The methanol-containing liquid stream produced as bottom product from column (E) is fed back to the reactor (B) via line (6) and compressor (F). Methyl formate (IV) is obtained as top product from the distillation column. The top product from the rectifying column (H) is passed via line (1) into a heat exchanger (C), in which entrained methyl formate and entrained methanol are condensed out. The remaining gas stream is fed back to the reactor via lines (2) and (3), with a device for purging waste gas (V) generally being present. The liquid condensed out in the heat exchanger (C) is fed to a condensate tank (D) via line (4), and methyl formate (IV) is obtained as product therefrom via line (5). Some of the condensed-out liquid is fed back to the rectifying column (H) as return via line (8).

It should be noted that it is possible for other apparatuses, for example a loop reactor, to be used instead of the bubble-column reactor in the process depicted in FIG. 3. Furthermore, both a non-cascaded reactor and a cascaded reactor can be employed in this variant.

The very particularly preferred process mentioned in the last paragraph has the particular advantage that some of the methyl formate can already be obtained in high purity via the rectifying column employed, and consequently further distillative work-up is generally unnecessary for this. This means that the methyl formate-containing stream obtained as bottom product from the rectifying column, which requires further distillative purification, is significantly reduced in amount, meaning that the distillation column necessary for this purpose can generally be designed smaller. These measures result in a simplification of the production plant and in particular, in running production, also in a significant saving of energy costs. The said process generally makes it possible to reduce the energy costs to about half compared to a process which does not use the said rectifying column.

The process according to the invention for the preparation of methyl formate is technically simple to carry out, results in only very little deposition of salt-like deposits, or none at all, requires only low equipment complexity, in particular owing to the low pressure compared with the known processes, has low energy consumption and low consumption of catalyst, and facilitates a space-time yield of methyl formate of $\geq 100$ g/lVh. The said advantages are achieved, in particular, by the high gas superficial velocity and the removal of gaseous methyl formate from the reactor.

EXAMPLES

Example 1

Example 1 was carried out using a pilot plant as depicted in FIG. 1. The reactor employed was a bubble column having an internal diameter of 55 mm and an overall height of 1000 mm.

In order to start up the plant, methanol (1.75 kg/h), carbon monoxide (1 kg/h) and catalyst solution (30% by weight solution of potassium methoxide in methanol in an amount which ensures a catalyst concentration of 1 mol/kg of liquid reaction mixture) were introduced and heated to 75° C., and the circulating-gas stream was put into operation. The circulating-gas stream was adjusted in such a way that the fill level in the bubble column was about 800 mm. The gas-treated volume was thus 1.9 l. When a pressure of 3.0 MPa abs. had been reached, the stated pressure was kept constant by regulating the waste gas valve.

During continuous operation, 1.75 kg/h of methanol, 1 kg/h of carbon monoxide and the requisite amount of 30% by weight solution of potassium methoxide in methanol to keep the catalyst concentration necessary were continued to be fed in. The catalyst consumption was about 1 kg of potassium methoxide per kg of ethyl formate formed. The circulating-gas ratio was 15 kg of circulating gas per kg of supplied fresh gas (i.e. 15 kg of circulating gas per hour). The mean molecular weight of the circulating gas was about 28 g/mol. The reaction temperature was 75° C. (measured at the upper end of the liquid level), and the reaction pressure was 30 MPa abs. The condensate obtained had a methyl formate content of about 65% by weight.

The gas flowed essentially in one direction, namely from bottom to top, throughout the bubble column. The cross-sectional area to be utilized for calculating the mean gas superficial velocity works out as $(5.5 \text{ cm}/2)^2 \cdot \pi = 23.8 \text{ cm}^2$. The overall flow rate of the gas flowing through this region is calculated from the circulating-gas flow rate and the flow rate of freshly supplied carbon monoxide gas, with the freshly supplied carbon monoxide flow rate only being calculated to the extent of one half owing to the consumption of carbon monoxide. The overall flow rate of gas flowing through was thus 15.5 kg/h, with the mean molecular weight being about 28 g/mol, the pressure being 3.0 MPa abs. and the temperature being 75° C. The volume flow rate of the gas flowing through is calculated from this as 148 cm$^3$/s. The mean gas superficial velocity was 6.2 cm/s.

A space-time yield of about 200 g of methyl formate per liter of gas-treated volume and per hour was obtained.

Example 1 shows that the process according to the invention enables a high space-time yield of about 200 g of methyl formate per liter of gas-treated volume and per hour to be obtained at a relatively low pressure of 3.0 MPa abs. and a relatively low reaction temperature of 75° C. The catalyst consumption of about 1 g of potassium methoxide per kg of methyl formate formed is likewise very low. Due to the relatively low pressure of 3.0 MPa abs. and the removal of gaseous methyl formate from the reactor, the process is technically simple and does not need complex equipment.

We claim:

1. A process for the preparation of methyl formate by reacting methanol with carbon monoxide at a pressure of from 0.5 to 10 MPa abs. in the presence of a metal alkoxide as catalyst in a reactor, in which a gas stream is withdrawn from the reactor, entrained methyl formate is removed from this gas stream by condensation, and all or some of the remaining gas stream is returned to the reactor as circulating-gas stream, which comprises setting a mean gas superficial velocity of from 1 to 20 cm/s in at least one region of the reactor in which the gas flows essentially in one direction, using potassium methoxide as catalyst and carrying out the reaction at a temperature of from 60 to 85° C.

2. A process as claimed in claim 1, wherein a mean gas superficial velocity of from 2 to 10 cm/s is set in at least one region of the reactor in which the gas flows essentially in one direction.

3. A process as claimed in claim 1, wherein the reaction is carried out at a concentration of catalyst employed of from 0.01 to 2 mol/kg of liquid reaction mixture.

4. A process as claimed in claim 1, wherein the reaction is carried out at a pressure of from 2 to 4 MPa abs.

5. A process as claimed in claim 1, wherein a molar ratio between the total amount of methanol fed to the reactor and the amount of freshly supplied carbon monoxide of from 1.4 to 3.3 is set.

6. A process as claimed in claim 1, wherein a bubble column is employed, and this is operated under co-current conditions with respect to the feed of the methanol-containing liquid stream and the carbon monoxide-containing gas stream.

7. A process as claimed in claim 1, wherein the reaction is carried out in a cascaded reactor.

8. A process as claimed in claim 7, wherein the uppermost zone of the cascaded reactor is operated at a temperature of from 80 to 150° C.

9. A process as claimed in claim 1, wherein the gas stream withdrawn from the reactor is separated in a rectifying column into a methyl formate-containing bottom stream and a carbon monoxide- and methyl formate-containing top stream, entrained methyl formate is removed from the top stream by condensation, and all or some of the remaining gas stream is fed back to the reactor as circulating-gas stream.

* * * * *